(12) United States Patent
Livolsi et al.

(10) Patent No.: US 7,959,080 B2
(45) Date of Patent: Jun. 14, 2011

(54) SYSTEM FOR PRINTING HOSPITAL LABELS AND WRISTBANDS

(75) Inventors: William R. Livolsi, Bridgeville, PA (US); James M. Scheid, Delaware, OH (US); Mark Snow, North Ridgeville, OH (US)

(73) Assignee: XPress Systems, LLC, Canonsburg, PA (US)

( * ) Notice: Subject to any disclaimer, the term of this patent is extended or adjusted under 35 U.S.C. 154(b) by 569 days.

(21) Appl. No.: 12/046,083

(22) Filed: Mar. 11, 2008

(65) Prior Publication Data

US 2009/0230179 A1 Sep. 17, 2009

(51) Int. Cl.
*G06K 7/00* (2006.01)

(52) U.S. Cl. .................. 235/435; 235/439; 235/462.01; 101/113; 400/73

(58) Field of Classification Search .................. 101/113; 400/82, 88; 235/435, 436, 454
See application file for complete search history.

(56) References Cited

U.S. PATENT DOCUMENTS

| | | |
|---|---|---|
| 3,831,006 A | 8/1974 | Chaffin, III et al. |
| 4,264,396 A | 4/1981 | Stewart |
| 4,476,381 A | 10/1984 | Rubin |
| 4,516,016 A | 5/1985 | Kodron |
| 4,552,608 A | 11/1985 | Hoffmann et al. |
| 4,628,193 A | 12/1986 | Blum |
| 4,652,317 A | 3/1987 | Seestrom |
| 4,706,096 A | 11/1987 | Sato |
| 4,746,932 A | 5/1988 | Sato |
| 4,846,924 A | 7/1989 | Morrison |
| 5,153,416 A | 10/1992 | Neeley |
| 5,166,498 A | 11/1992 | Neeley |
| 5,229,584 A | 7/1993 | Erickson |
| 5,239,622 A | 8/1993 | Best et al. |
| 5,483,624 A | 1/1996 | Christopher et al. |
| 5,520,470 A | 5/1996 | Willett |
| 5,524,184 A | 6/1996 | Johnson |
| 5,602,377 A | 2/1997 | Beller et al. |
| 5,781,708 A | 7/1998 | Austin et al. |
| 5,805,779 A | 9/1998 | Christopher et al. |
| 5,839,836 A | 11/1998 | Yuyama et al. |
| 5,884,273 A | 3/1999 | Sattizahn et al. |
| 5,888,087 A | 3/1999 | Hanson et al. |
| 5,924,074 A | 7/1999 | Evans |
| 5,963,453 A | 10/1999 | East |
| 5,988,898 A * | 11/1999 | Ackley ........................... 400/61 |
| 6,170,746 B1 | 1/2001 | Brook et al. |
| 6,318,630 B1 | 11/2001 | Coughlin et al. |
| 6,318,631 B1 | 11/2001 | Halperin |
| 6,379,059 B2 | 4/2002 | Kaplan |
| 6,519,569 B1 | 2/2003 | White et al. |
| 6,663,006 B2 | 12/2003 | Mullins et al. |
| 6,666,377 B1 | 12/2003 | Harris |
| 6,687,016 B2 | 2/2004 | Gauthier |
| 6,714,983 B1 | 3/2004 | Koenck et al. |
| 6,744,938 B1 | 6/2004 | Rantze et al. |
| 6,793,334 B2 | 9/2004 | Blackman et al. |
| 7,344,078 B2 * | 3/2008 | Elliott et al. ............. 235/462.01 |

(Continued)

*Primary Examiner* — Thien M. Le
*Assistant Examiner* — Christie I Marshall
(74) *Attorney, Agent, or Firm* — Eckert Seamans Cherin & Mellott, LLC; David C. Jenkins, Esquire

(57) ABSTRACT

A system for printing hospital labels and wrist bands having a capture station, wherein a master label is created, and multiple independent label stations, wherein additional labels may be printed based solely on information in the master label, without being connected to a data network.

17 Claims, 4 Drawing Sheets

U.S. PATENT DOCUMENTS

| | | |
|---|---|---|
| 2003/0031340 A1 | 2/2003 | Alattar et al. |
| 2003/0112471 A1 | 6/2003 | Damera-Venkata et al. |
| 2003/0121615 A1 | 7/2003 | Gravelle et al. |
| 2003/0144878 A1 | 7/2003 | Wilkes et al. |
| 2004/0046026 A1 | 3/2004 | Krampitz et al. |
| 2004/0078231 A1 | 4/2004 | Wilkes et al. |
| 2004/0108381 A1* | 6/2004 | Elliott et al. ............ 235/462.01 |
| 2004/0118923 A1 | 6/2004 | Creamer et al. |
| 2004/0128162 A1 | 7/2004 | Schlotterbeck et al. |
| 2004/0133705 A1 | 7/2004 | Broussard et al. |
| 2004/0205067 A1* | 10/2004 | Veidung ........................ 707/10 |
| 2004/0215486 A1 | 10/2004 | Braverman |
| 2007/0284449 A1* | 12/2007 | Yuen ....................... 235/462.45 |

\* cited by examiner

SYSTEM FOR PRINTING HOSPITAL LABELS AND WRISTBANDS

BACKGROUND OF THE INVENTION

1. Field of the Invention

This invention relates to a system for printing hospital labels and wrist bands, and more specifically, to a system having a capture station, wherein a master label is created, and multiple independent label stations, wherein additional labels may be printed based solely on information in the master label, without being connected to a data network.

2. Background Information

To improve efficiency, hospitals adopted a system, wherein each patient was given an embossed plastic card (much like a normal credit card), which was used to imprint multi-part forms. The embossed card included information, such as the patient's name, the patient's account number, medical record number, and doctor's name, as well as other patient demographic information. The embossed card was kept at a central location and made available to all medical personnel responsible to the patient. With any patient charting, medical procedure, or lab specimen that was taken, a form would first be imprinted with the information from the patient's embossed card, which would transfer the information contained on the embossed card to the form, label, or wristband using the ink roller on the imprinter for the top form and carbon or carbonless sheets for the underlying sheets. Then, the multiple copies of the form would be taken apart and the pages placed in the patient's chart and sent to various departments within the medical facility for record keeping and billing purposes. The multi-part forms were structured to be run through a motorized electric imprinter. The embossed card would be placed on the imprinter's anvil and the form placed over the top of the embossed card. The lid or top of the imprinter would be closed and the imprinter's motor would drive a hard ink roller across the anvil and transfer the embossed card information to each page of the multi-part form. This basic system, however, had many disadvantages. The embossing machines and the imprinting machines are both large and expensive. Additionally, the imprinting machine did not always function properly, whereby forms would be imprinted illegibly or torn and have to be prepared again.

It was desirable to have a label system structured to create labels which could be attached to the forms. These labels would contain the same or similar information as the embossed card and provide added features not possible with the embossed card system. One form of labeling system utilizes a small special-purpose computer with a built-in magnetic stripe reader, a printer, and card embosser with magnetic stripe encoding capabilities, and plastic cards with a magnetic stripe. The magnetic stripe on the card contains the encoded patient information. When the card with the magnetic stripe was inserted into the stripe reader, the information in the magnetic stripe was read, and a label was printed with the patient information. The disadvantage to the magnetic card system is that the magnetic stripe reading equipment is expensive. Additionally, the magnetic stripe can only contain a small amount of information that can be encoded onto the stripe.

Another system utilized printer stations coupled to a network. Data was input at the individual computer workstations by hospital personnel, and by sending printer commands over the network, a printed label was produced. This system, however, required that there be a network connection, meaning a hardwire or a wireless connection, at each location where a label printer was required to be, along with an accessible computer workstation that would give the access to send the information to the printer. Many hospitals, especially older hospitals, do not have enough network access ports in all locations where a label printer is required. Installing network access ports can involve a large financial expense for each additional port required for the label printers. Other systems, coupled to the hospital's network, utilize a laser printer to print out pages of labels for a single patient. In many cases, these labels were wasted as patient labels did not often require an entire sheet of patient printed labels. Additionally, the extra labels that are not used need to be shredded since they contain confidential patient information. These sheet labels are also damaging to the laser printers and can damage expensive internal components if the labels from the pages come off and adhere inside the printer.

SUMMARY OF THE INVENTION

These needs, and others, are met by the present invention which provides a system for printing hospital labels and wrist bands having a capture station, wherein a master label is created, and multiple independent label stations, wherein additional labels may be printed based solely on information in the master label, i.e., without being connected to a data network. The capture station includes a housing enclosing an electronic control device, e.g., a programmable logic circuit, associated memory, and one or more routines/programs stored therein, having at least a keyboard input, and preferably, a network connection, a keyboard, and a printer assembly, preferably a thermal printer or a thermal transfer printer. The capture station is structured to produce a Master Barcode Label, which is an encoded bar code and which, preferably, includes additional human readable text. Preferably, the Master Barcode Label utilizes a 2-D barcode and includes encoded data relevant to the patient. That is, the encoded data includes the data that is to be reproduced on subsequently printed patient label. This, typically includes the patient's name and an identification number as well as a date of birth and/or date of admission. The encoded data may also include additional information that is not typically printed on a patient label, for example, the patient's blood type, allergies, treating physician, or other information.

The patient data is, preferably, transmitted via the network to the capture station; however, if the network connection is not available or otherwise interrupted, a nurse may enter the patient data via the keyboard. Data transmitted by the network may be in the format used with the traditional hospital embossing machines. The electronic control device converts the patient data into the encoded format and sends an instruction to the thermal printer to print one or more Master Barcode Labels with the encoded bar code. Further, for additional security, the patient data may be encrypted while in a binary form, i.e., before the patient data is printed as an encoded barcode.

The Master Barcode Label, as well as subsequently printed patient labels, may include "fixed printing." Fixed printing is text and/or a graphic printed on every label regardless of the patient data. Fixed printing would typically be the name of the hospital or treatment facility. The fixed printing is incorporated into the program that controls the printing assembly.

After the Master Barcode Label is printed, it accompanies the patient wherever the patient travels within the hospital. For example, one Master Barcode Label may be placed on, or otherwise incorporated into, the patient's wristband and another Master Barcode Label may be placed on a card, or any other label carrier, attached to the patient's chart. The capture station can also be configured to produce finished patient labels along with the Master Barcode Label so the hospital staff can label patient forms at the time the Master Barcode Label is created.

Once a patient is at a location away from the capture station, e.g., in his/her room, a test facility, operating room, or other remote location, additional patient labels may be printed at a label station using the data stored on the Master Barcode Label. The label station includes a housing enclosing an electronic control device, e.g., a programmable logic circuit, associated memory and one or more routines/programs stored therein structured to operate the label station, a printer assembly, and a scanner. The label station is not coupled to a network and does not include a storage device sufficient to store patient data. That is, the label station associated memory has a sufficient capacity to store/execute the routines and programs necessary to operate the label station, but does not have a sufficient memory to store a plurality of patient records or other data.

The label station electronic control device is structured to be, and is, in electronic communication with the printer and the scanner. In operation, a nurse scans the Master Barcode Label, whereupon the data in the Master Barcode Label is converted to an electronic signal. As is known, the scanning device is typically structured to interpret the encoded barcode. As such, the data in the signal represents the patient data or, as noted above, the patient data in an encrypted form. The electronic signal is transmitted to the label station electronic control device. If the scanner is not structured to interpret the encoded barcode, the label station electronic control device interprets the signal, that is, decodes the information in the Master Barcode Label. Further, if the binary form of the patient data was encrypted, the label station electronic control device also interprets the encrypted data so that the patient data is returned to a raw form, such as, but not limited to ASCII data. The interpreted patent data is provided to the printer assembly. That is, the label station electronic control device instructs the printer to print one or more additional Master Barcode Label and/or patient labels.

The additional patient labels include human readable text and may include a barcode and any fixed printing, as noted above. Thus, the label station, without a network connection and without storing patient data, is able to print a patient label based upon the data interpreted from the encoded Master Barcode Label. It is noted that data interpreted from a Master Barcode Label merely passes through the label station electronic control device. That is, after the label station prints the additional labels, the patient data is deleted from the label station electronic control device. In essence, the label station is a "print and forget" device with regard to patient data. Because the label station only requires power, multiple label stations may be placed at different locations throughout the hospital without the need for any computer network connection.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

As used herein, the word "nurse" shall mean any health care professional or administrator who works with patient paperwork.

As used herein, a "patient label" is a label that includes human readable alphanumeric text and may include a barcode or fixed printing.

As used herein, "interpret" means to convert from one language to another including converting from an encrypted form to a non-encrypted form. That is, reading or observing an image and reproducing that image does not require interpretation. Thus, a copy machine does not "interpret" an image. Further, "interpret" means to produce, or allow another device to produce, the image in the second language. Thus, a copy machine or a scanner structured to reproduce images does not "interpret" an image even if during the copying process the image is stored, processed, and/or converted to an electronic form by the copy machine or scanner.

As used herein, a "network connection" means a physical connection, i.e. a hardwired connection, as well as a wireless connection.

As used herein, a "significant storage device" is an electronic storage device structured to store a plurality of patient records in a non-transitory manner. Significant storage devices include, but are not limited to, hard drives and magnetic tape storage devices.

Figure 1:
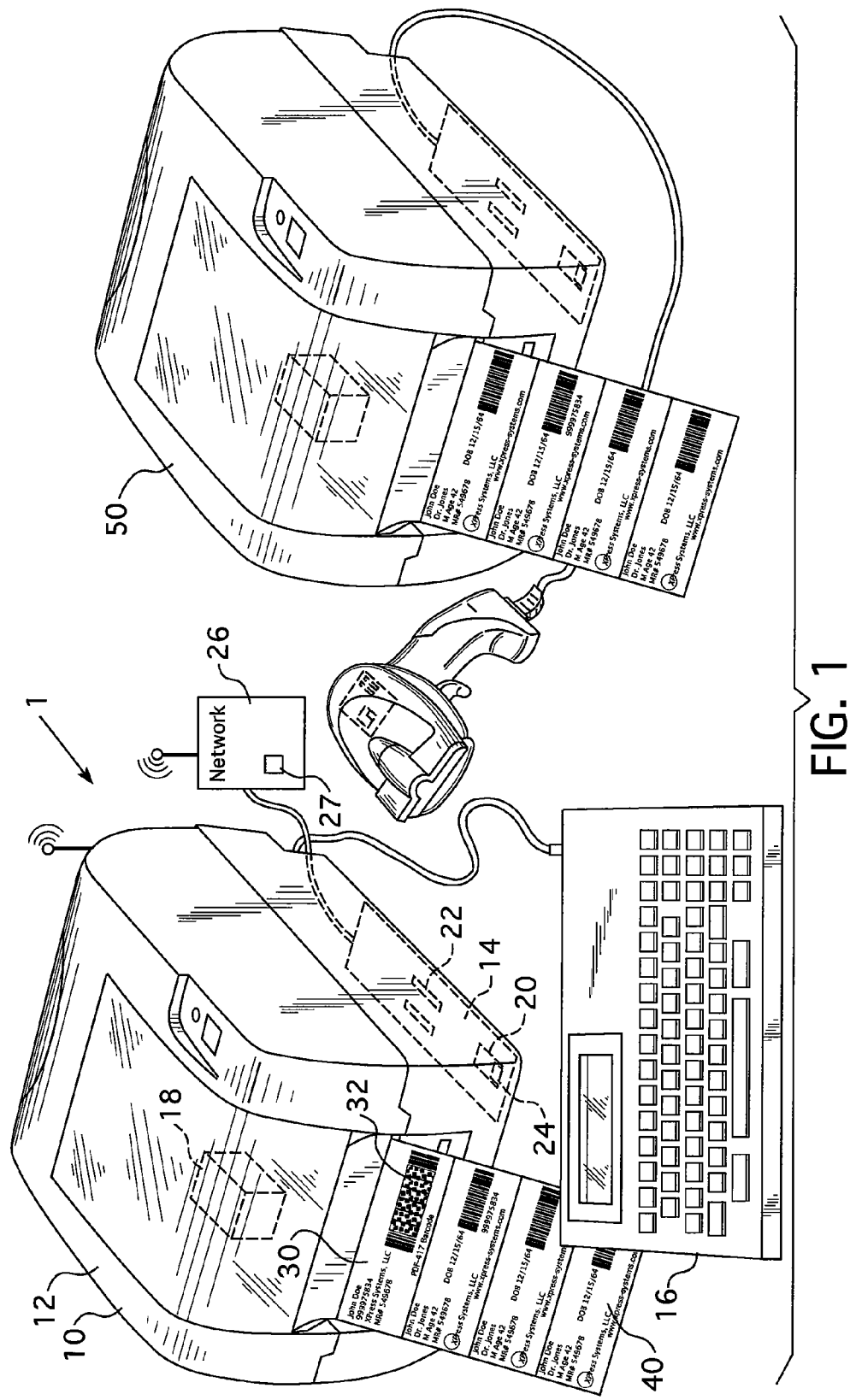
FIG. 1 is an isometric view of the electronic label system focusing on the capture station.

An electronic label system 1, includes a capture station 10, and a label station 50. As shown in FIG. 1, the capture station 10 includes a housing 12 enclosing an electronic control device 14, a keyboard 16, and a printer assembly 18 (shown schematically), preferably a thermal printer or thermal transfer printer. The capture station electronic control device 14 includes a programmable logic circuit 20, associated memory 22, and one or more routines/programs 24 (shown schematically) stored therein. As shown, the capture station electronic control device 14 is, preferably, enclosed in the same housing 12 as the printer assembly 18. It is understood that these components may each have their own housing 12. The capture station electronic control device 14 is structured to be, and is, in electronic communication with the keyboard 16 and capture station printer assembly 18, as well as an electronic data network 26 (shown schematically). The electronic data network 26 is structured to provide patient data 27 to the capture station 10. However, if the network connection is not available or otherwise interrupted, a nurse may enter patient data 27 via the keyboard 16. That is, the keyboard 16 is structured to provide manual input of patient data 27. Patient data 27 transmitted by the electronic data network 26 may be in the format used with the traditional hospital embossing machines, that is, a non-encoded format.

Figure 2:
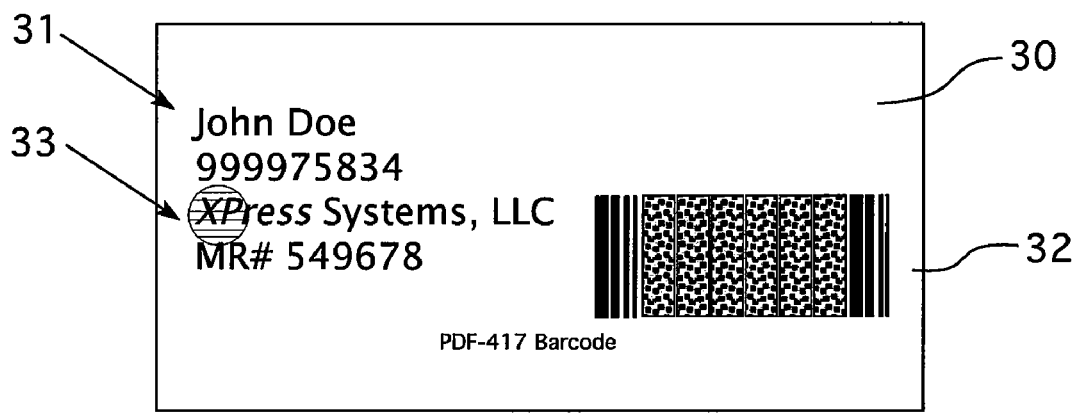
FIG. 2 a view of a Master Barcode Label with an encoded bar code.
Figure 3:
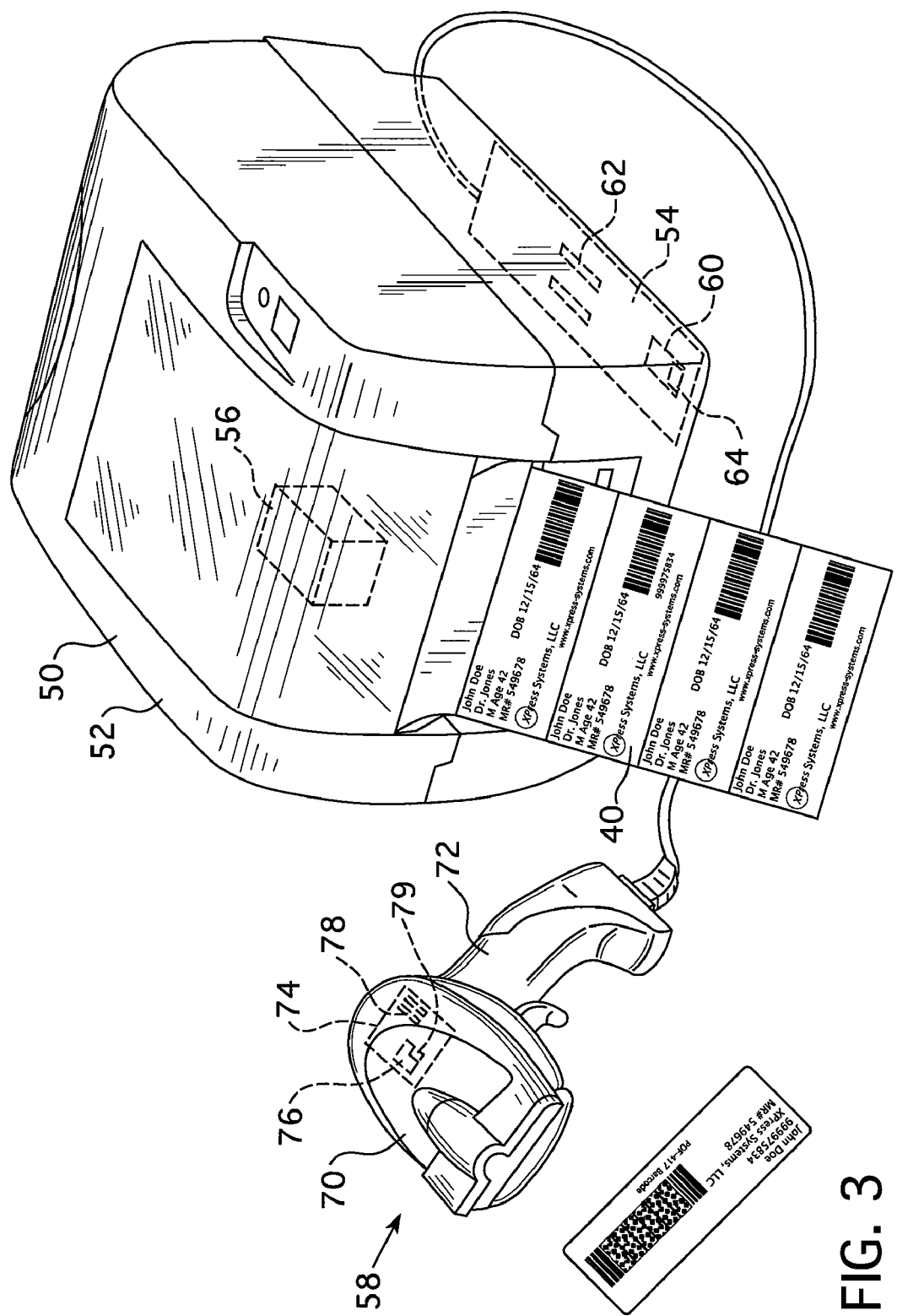
FIG. 3 is an isometric view of a label station.

The capture station electronic control device 14 converts the patient data 27 into an encoded format and sends an instruction to the capture station printer assembly 18 to print at least one Master Barcode Label 30 with the encoded bar code 32 as shown in FIG. 2. The encoded bar code 32 is, preferably, a 2-D encoding format, such as, but nor limited to PDF417, QR Code, Data Matrix, Data Strip, Aztec Code, Maxicode, Micro PDF417, or Micro QR Code. The Master Barcode Label 30 may also include human readable alphanumeric text 31 and/or fixed printing 33. The capture station electronic control device 14 may also encrypt the patient data 27 prior to converting the patient data 27 into the encoded format. That is, the patient data 27 may be encrypted in a binary format prior to converting the patient data 27 into the encoded format used in the encoded bar code 32.

The capture station 10 can also be configured to produce patient labels 40, discussed below, along with the Master Barcode Label 30 so the hospital staff can label patient forms at the time the Master Barcode Label 30 is created. Thus, the capture station 10 is structured to print a Master Barcode Label 30 based upon a non-encoded input. The Master Barcode Label 30 is printed on an adhesive label and placed on a carrier, such as, but not limited to, a wristband or card attached to the patient's chart. The Master Barcode Label 30 then accompanies the patient wherever the patient travels within the hospital or related facilities. Of course, the Master Barcode Label 30 may be printed directly on to the carrier or other substrate.

Figure 4:
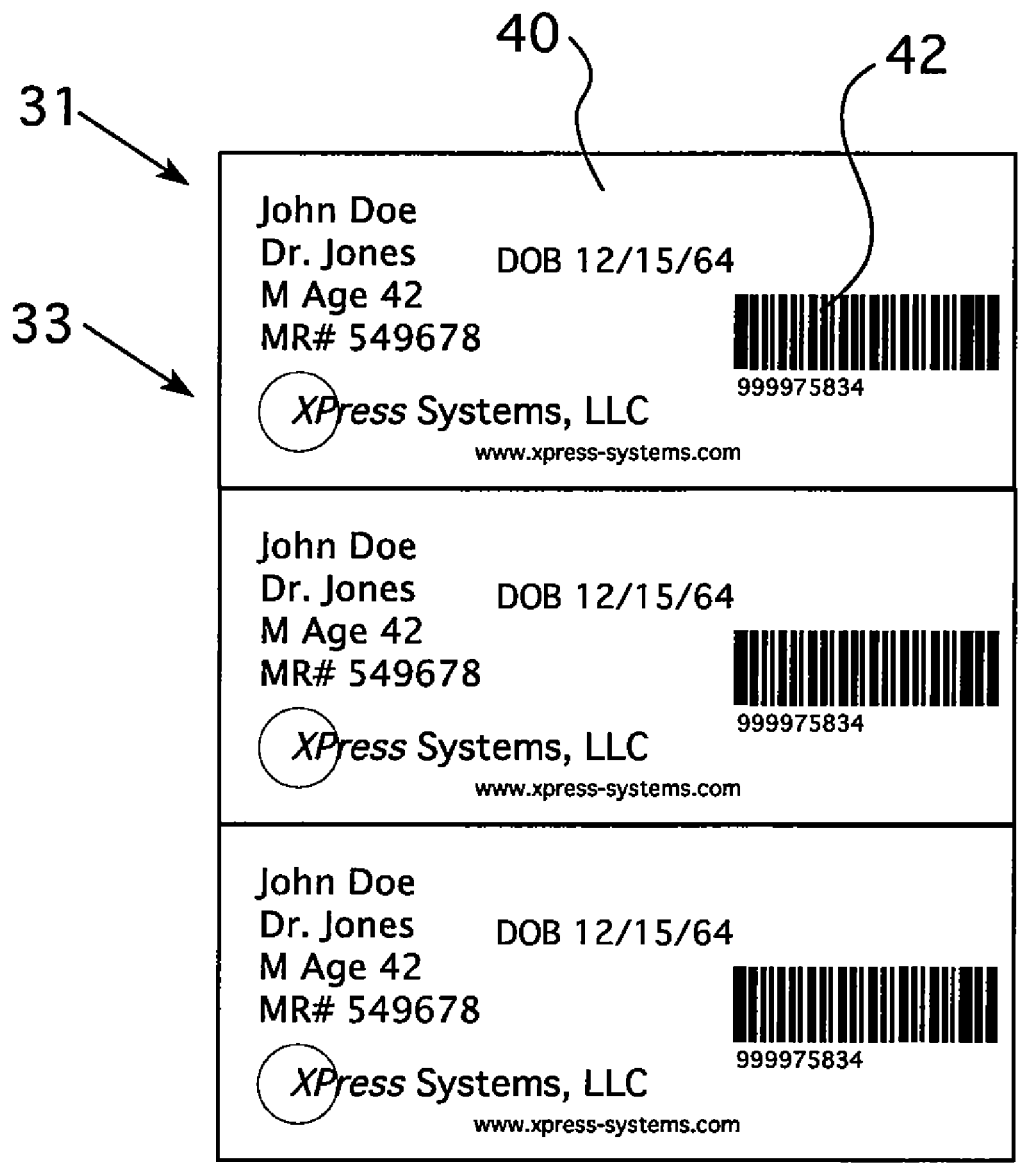
FIG. 4 a view of a Patient Label with human readable text.

After the Master Barcode Label 30 is created, the patient will typically be moved to another area of the hospital or a related facility, hereinafter a "remote location." The patient's wristband, and/or other label carrier, with a Master Barcode Label 30 accompanies the patient. The remote locations of the hospital may not have access to the electronic data network 26. The hospital, however, typically needs to have patient labels 40 created at the remote locations to be applied to various forms and specimens. As shown in FIG. 4, a patient label 40 includes human readable alphanumeric text 31, such as the patient's name, the patient's doctor's name, a patient number, or other basic information. The patient label 40 may also include a bar code 42, and encoded bar code 32, or fixed printing 33.

Accordingly, a label station 50 includes a housing 52 enclosing an electronic control device 54, a printer assembly 56, and a scanner 58. As with the capture station electronic control device 14, the label station electronic control device 54 includes a programmable logic circuit 60, associated memory 62, and one or more routines/programs 64 stored therein structured to operate the label station 50. Further, the label station electronic control device 54 is structured to be, and is, in electronic communication with the printer assembly 56 and scanner 58.

Unlike capture station electronic control device 14, however, label station electronic control device 54 is not coupled to the electronic data network 26. Further, label station electronic control device 54 does not include a significant storage device. That is, the label station electronic control device 54 is limited to an amount of memory 62 and one or more routines/programs 64 (shown schematically) sufficient to operate the label station 50 and does not have a sufficient memory to store data relating multiple patient records. Thus, the label station 50 is a "stand alone" device, wherein any data or information not related to the operation of the label station 50, specifically, any patient data, must be provided from an outside source. Accordingly, the label station 50 is structured to receive encoded data and interpret that data into another language, such as, but not limited to, human readable text and non-encoded barcodes. Thus, as detailed below, the label station 50 is structured to interpret encoded data from a Master Barcode Label 30 and print a patient label 40, or another Master Barcode Label 30, based upon that encoded input.

The label station printer assembly 56 is, preferably, a thermal printer or thermal transfer printer and may be substantially similar to the capture station printer assembly 18. The scanner 58 may include a scanning unit 70, such as, but not limited to a hand-held scanner 72. The scanner 58 may also be fixed (not shown) to the label station 50. As is known in the art, the scanner 58 includes an electronic control means 74 having a programmable logic circuit 76, associated memory 78, and one or more routines/programs 79 (shown schematically) stored therein structured to operate the scanner 58. The scanner electronic control means 74 is, typically, structured to interpret the encoded bar code 32 and convert the data from the encoded bar code 32 into an electronic signal. This signal may be raw data, such as, but not limited to ASCII data, or, as noted above, may be encrypted binary data. As set forth above, the label station electronic control device 54 is structured to receive this signal from the scanner 58. If the scanner 58 did not interpret the data and/or if the data is in an encrypted binary form, the label station electronic control device 54 is structured to interpret that data into another language, preferably a human readable language.

The label station electronic control device 54 further converts the interpreted data into a format that may be printed as a patient label 40. This interpreted data is transmitted to the label station printer assembly 56, whereupon a patient label 40 is printed. The patient label 40 is, preferably, printed on a substrate, such as an adhesive label coupled to a removable backing. The label station electronic control device 54 may be programmed to print one or more patient labels 40 each time the label station printer assembly 56 is activated; that is, for example, if the user typically fills out forms in triplicate, the label station electronic control device 54 may be programmed to always print three labels. The label station 50 may also be structured to print Master Barcode Labels 30.

In operation, the label station 50 may be set up at any location where there is a power source and is typically set up at a nurse's station or may be portable. When a patient is admitted to a hospital, one or more Master Barcode Labels 30 are made as described above. For example, when a procedure tracked by form paperwork is performed, a nurse prepares the paperwork except for the patient data 27. The patient data 27 is provided by the label station 50; that is, the nurse acquires a Master Barcode Label 30 and utilizes the label station 50 to print one or more patient labels 40. To do this, the nurse presents the Master Label Barcode 30 to the scanner 58. The scanner 58 scans the Master Barcode Label 30, and more specifically, the encoded barcode 32, and creates an electronic signal carrying data representative of the information on the Master Barcode Label 30. The electronic signal carrying data is transmitted to the label station electronic control device 54. The label station electronic control device 54 interprets the electronic signal carrying data and further directs the label station printer assembly 56 to print one or more patient labels 40. The nurse then applies the patient label(s) 40 to the paperwork forms.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

What is claimed is:

1. An electronic label system comprising:
   a capture station structured to print a Master Barcode Label based upon a non-encoded input;
   said Master Barcode Label having encoded data printed thereon; and
   a label station structured to interpret encoded data from said Master Barcode Label and print a patient label based upon said encoded data.

2. The electronic label system of claim 1 wherein said label station is not coupled to an electronic network and does not include a memory structured to store patient data.

3. The electronic label system of claim 2 wherein said capture station includes a network connection and is in communication with an electronic network.

4. The electronic label system of claim 3 wherein:
said label station includes an electronic control device, a printer, and a scanner; and
said label station electronic control device structured to be in electronic communication with said label station printer and scanner; and
wherein said scanner is structured to read said Master Barcode Label, and said label station electronic control device structured to convert the interpreted data into a format that may be printed by said label station printer as a patient label.

5. The electronic label system of claim 4 wherein:
said capture station is structured to receive patient data from said electronic network; and
said capture station is structured to encrypt said patient data prior to printing said Master Barcode Label.

6. The electronic label system of claim 5 wherein said label station electronic control device is structured to interpret encoded data from said Master Barcode Label.

7. The electronic label system of claim 5 wherein:
said scanner is structured to interpret, but not decrypt, encoded data from said Master Barcode Label and convert said data into an electronic signal; and
said label station electronic control device is structured to decrypt said encoded data from said Master Barcode Label.

8. The electronic label system of claim 3 wherein said label station electronic control device does not include a significant storage device.

9. The electronic label system of claim 2 wherein:
said capture station includes an electronic control device, a keyboard, and a printer;
said capture station electronic control device in electronic communication with said keyboard, capture station printer, and electronic data network;
wherein said electronic data network is structured to provide patient data to the capture station; and
said capture station electronic control device is structured to convert said patient data into an encoded format and send an instruction to said capture station printer assembly to print at least one Master Barcode Label with an encoded bar code.

10. The electronic label system of claim 9 wherein said patient data transmitted by the electronic data network is in the format used with traditional hospital embossing machines.

11. The electronic label system of claim 10 wherein said keyboard is structured to provide manual input of patient data.

12. The electronic label system of claim 9 wherein:
said label station includes an electronic control device, a printer, and a scanner; and
said label station electronic control device structured to be in electronic communication with said label station printer and scanner; and
wherein said scanner is structured to read said Master Barcode Label, and said label station electronic control device structured to convert the interpreted data into a format that may be printed by said label station printer as a patient label.

13. The electronic label system of claim 12 wherein:
said capture station is structured to receive patient data from said electronic network; and
said capture station is structured to encrypt said patient data prior to printing said Master Barcode Label.

14. The electronic label system of claim 13 wherein said label station electronic control device is structured to interpret encoded data from said Master Barcode Label.

15. The electronic label system of claim 14 wherein:
said scanner is structured to interpret, but not decrypt, encoded data from said Master Barcode Label and convert said data into an electronic signal; and
said label station electronic control device is structured to decrypt said encoded data from said Master Barcode Label.

16. The electronic label system of claim 14 wherein said label station electronic control device does not include a significant storage device.

17. The electronic label system of claim 1 wherein said label station does not include a significant storage device.

* * * * *